(12) United States Patent
Hernandez Juanpera

(10) Patent No.: US 10,245,059 B2
(45) Date of Patent: Apr. 2, 2019

(54) TOOL AND GRIP DEVICE PROVIDED WITH SAID TOOL

(71) Applicant: Servocad Microtronics S.L., Manresa (ES)

(72) Inventor: Jesus Hernandez Juanpera, Manresa (ES)

(73) Assignee: Servocad Microtronics S.L., Manresa (ES)

( * ) Notice: Subject to any disclaimer, the term of this patent is extended or adjusted under 35 U.S.C. 154(b) by 239 days.

(21) Appl. No.: 15/303,742

(22) PCT Filed: Apr. 10, 2015

(86) PCT No.: PCT/ES2015/070282
§ 371 (c)(1),
(2) Date: Oct. 13, 2016

(87) PCT Pub. No.: WO2015/158945
PCT Pub. Date: Oct. 22, 2015

(65) Prior Publication Data
US 2017/0027598 A1  Feb. 2, 2017

(30) Foreign Application Priority Data

Apr. 17, 2014 (ES) .................................. 201430577

(51) Int. Cl.
*A61B 17/00*  (2006.01)
*A61B 17/29*  (2006.01)
*A61B 34/00*  (2016.01)

(52) U.S. Cl.
CPC .............. *A61B 17/29* (2013.01); *A61B 34/70* (2016.02); *A61B 34/72* (2016.02);
(Continued)

(58) Field of Classification Search
CPC ......... A61B 34/70; A61B 34/72; A61B 17/29; A61B 2017/00398; A61B 2017/2944;
(Continued)

(56) References Cited

U.S. PATENT DOCUMENTS

2006/0047278 A1 * 3/2006 Christian ........... A61B 18/1442
606/41
2006/0111735 A1 * 5/2006 Crainich ................ A61B 17/12
606/157

(Continued)

*Primary Examiner* — Katrina M Stransky
(74) *Attorney, Agent, or Firm* — Thedford I. Hitaffer; Hitaffer & Hitaffer, PLLC

(57) ABSTRACT

The invention relates to a tool including a pair of jaws (3) interacting with one another by means of actuating means comprising a central stationary portion and two cam plates (4) arranged such that said plates are facing both sides of the central stationary part, which are slidable on said central stationary part. The two cam plates being associated with a shaft for driving linear movement, the jaws being coupled to the central stationary part and the two cam plates (4). Thus, during a forward movement of the cam plates, said plates cause a linear movement away from one jaw respective to the other, during a backward movement thereof, said cam plates (4) cause a linear movement for moving one of the jaws (3) closer to the other.

18 Claims, 6 Drawing Sheets

(52) U.S. Cl.
CPC ............... *A61B 2017/00398* (2013.01); *A61B 2017/2936* (2013.01); *A61B 2017/2944* (2013.01)

(58) Field of Classification Search
CPC ........ A61B 2017/2936; A61B 18/1445; A61B 18/1447; A61B 2018/145; B25J 7/00
See application file for complete search history.

(56) References Cited

U.S. PATENT DOCUMENTS

2006/0271042 A1* 11/2006 Latterell ............ A61B 18/1445
606/51
2012/0172924 A1* 7/2012 Allen, IV ............... A61B 17/29
606/205

* cited by examiner

TOOL AND GRIP DEVICE PROVIDED WITH SAID TOOL

RELATED APPLICATIONS

This application is a National Phase of PCT Patent Application No. PCT/ES2015/070282 having International filing date of Apr. 10, 2015, which claims the benefit of Spanish Patent Application No. P201430577 filed on Apr. 17, 2014. The contents of the above applications are all incorporated by reference as if fully set forth herein in their entirety.

OBJECT OF THE INVENTION

The object of the present application for patent of invention is to file a tool that incorporates significant innovations and advantages.

More specifically, the invention proposes the development of a tool, for example, for medical applications, comprising a pair of jaws that interact with one another by means of actuating means, which makes it possible to simplify the construction process and reduce manufacturing costs, and a grip device provided with said tool.

FIELD AND BACKGROUND OF THE INVENTION

Surgical grip devices equipped with a manually actuated pair of jaws arranged on a support structure are well known in the current state of the art, whose operation is based essentially on the fact that the two jaws are articulated at a pivot point that enables the angular movement thereof to perform opening and/or closing operations.

American patent number US2006182606 discloses a tool for handling or gripping very small materials based on the angular movement of the jaws. This angular movement implies a larger work area which, depending on the application of these jaws, may complicate their use. Additionally, depending on the application of the tool, this pivotal movement of the jaws may reduce the work precision required in accordance with the objects or region of a human being to be handled.

The existence of a tool envisaged, for example, to form part of a laparoscopic surgical instrument wherein the two jaws perform a non-angular linear movement to perform separation operations (separation condition) or approximation operations (gripping condition) of the jaws with an assembly composed of a small number of components that enable the execution of the linear movement.

SUMMARY OF THE INVENTION

The present invention has been developed with the aim of providing a tool that is a novelty within the field of application and resolves the aforementioned drawbacks, as well as providing other additional advantages that will become evident from the description hereunder.

Therefore, an object of the present invention is to provide a tool that comprises a pair of jaws that interact with one another by means of actuating means and is characterised in that said actuating means comprise a central stationary part and two cam plates, arranged such that said plates are facing both sides of the central stationary part, which are slidable on said central stationary part. The two cam plates are associated with a shaft for driving linear movement and wherein the jaws are coupled to the central stationary part and on the two cam plates.

These characteristics make it possible to obtain a system with a simplified structure that enables the opening and closing movement of a pair of jaws, wherein the movement of said jaws is carried out in parallel relationship therebetween at all times, i.e. there is no pivot point between the two jaws, due to which it is adequate for surgical operations. In turn, this simplicity of construction makes it possible to easily and quickly replace the jaws.

Thus, during a forward movement of the cam plates, said plates cause a linear movement away from one jaw respective to the other, whereas during a backward movement thereof, said cam plates cause a linear movement for moving one of the jaws closer to the other.

According to another aspect of the invention, each of the cam plates has a pair of upper linear slots and a pair of lower linear slots that converge respectively at a point near the central longitudinal axis of the plate, in whose upper and lower grooves protuberances that project from each of the jaws are slidable. These plates can be easily manufactured in large quantities.

In accordance with the invention, the central stationary part comprises a substantially U-shaped body wherein each of its side flaps include a pair of upper grooves and a pair of lower grooves wherein protuberances that project from each of the jaws are slidable, said grooves extending from a central part of the side flaps in the direction of the upper and lower rim, respectively.

Preferably, the two cam plates are joined to one another by means of a single intermediate piece coupled to the linear actuation axis, said intermediate piece being movable through guiding means arranged on the central stationary part.

In a preferred embodiment, the guiding means consist of a window arranged on each of the flaps of the substantially U-shaped body.

Additionally, the intermediate piece and the two cam plates have additional fixing means, said fixing means preferably comprising through holes disposed in the intermediate piece and the two cam plates, wherein a pin or screw element is inserted.

Advantageously, the tool has elastic means arranged between the two jaws, for example, a helical spring housed in the central stationary part.

Another object of the invention is to provide a grip device, particularly envisaged for precision handling of small objects, such as a body tissue of a human being or animal, which comprises actuating means associated with a tool such as that described previously.

Preferably, the actuating means include electrically motorised means.

Advantageously, the grip device of the invention includes a user interface connected to the actuating means which allows handling of the two jaws.

According to another aspect of the invention, the actuating means include a rotating shaft solidly coupled to the central stationary part. Therefore, the tool is capable of rotating upon itself and simultaneously performing the opening and/or closing actions of the jaws.

Preferably, the rotating shaft is internally hollow, in whose interior the shaft for driving the linear movement is housed, due to which the rotating and linear movements are enabled through a single outlet hole in an external housing. This reduces the risk of fluids entering the interior of the grip device or Advantageously, the grip device may include removable blocking means for maintaining the central stationary part joined to the rotating shaft. In a particular embodiment, these blocking means consist of a pin fitted on one end with a grip section, insertable in a circumferentially slotted section in the central stationary part of the actuating means and a tightening rotating wheel.

According to another aspect of the invention, the rotary movement of the rotating shaft of the actuating means is transmitted by means of a gear assembly formed by two cogwheels that engage with each other, wherein each cogwheel is associated with an independent actuator.

Preferably, the actuating means include a printed circuit board connected to the user interface.

Other characteristics and advantages of the tool object of the present invention will become evident from the description of a preferred, but not exclusive, embodiment illustrated by way of non-limiting example in the accompanying drawings, wherein:

DESCRIPTION OF SPECIFIC EMBODIMENTS OF THE INVENTION

In view of the aforementioned figures and in accordance with the numbering adopted, an example of a preferred embodiment of the invention can be observed therein, comprising the parts and elements indicated and described in detail below.

Figure 1:
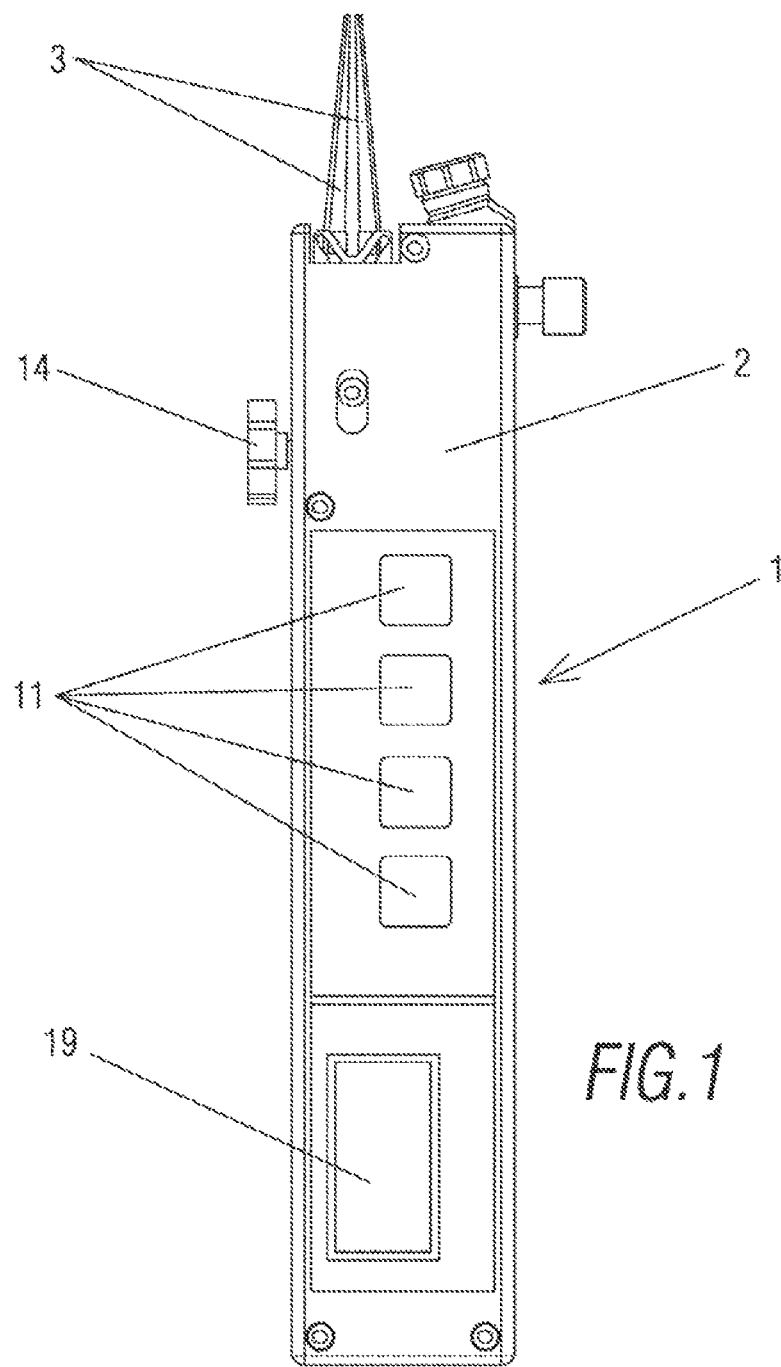
FIG. 1. Shows a side elevational view of an embodiment of a grip device in accordance with the present invention.
Figure 2:
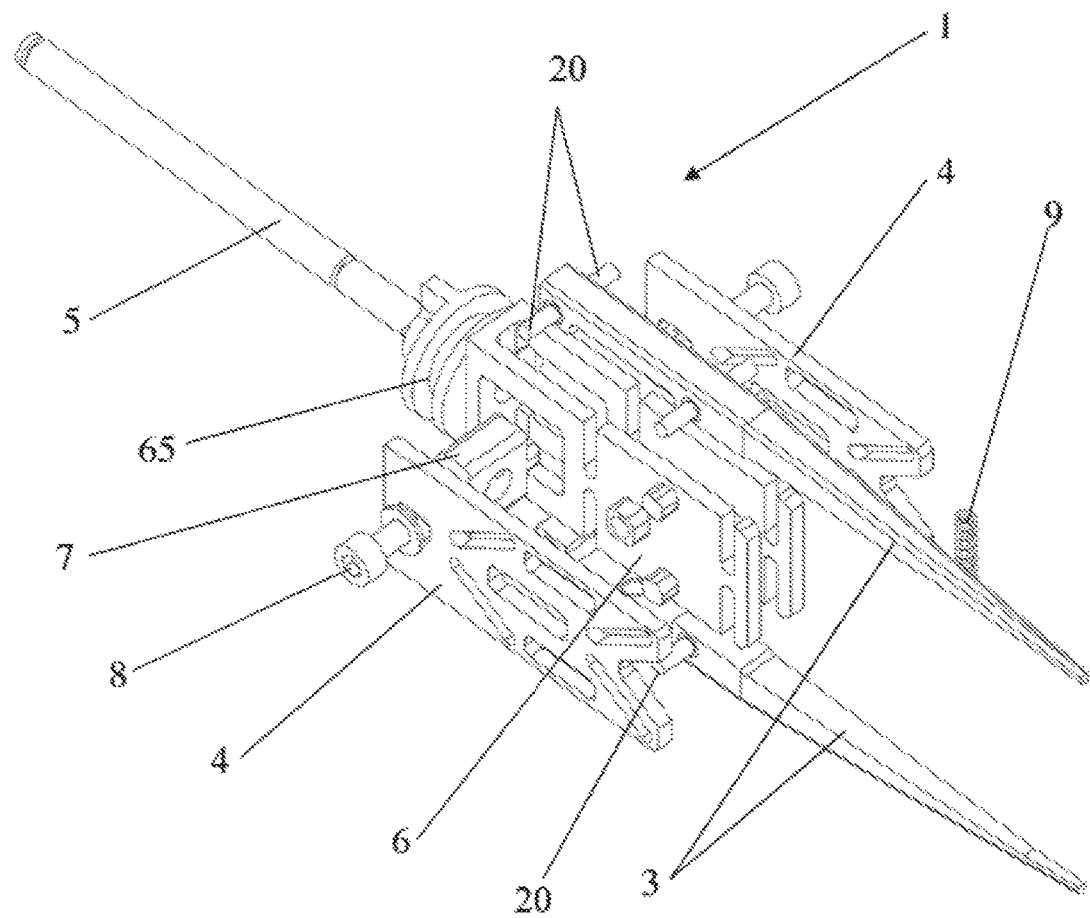
FIG. 2. Shows an exploded perspective view of the tool of the invention.

Therefore, as can be observed in FIG. 1, a grip device is disposed, indicated in general by reference (1), which is specially envisaged to perform precision handling of small objects, that comprises a grip section formed by an outer housing (2) made of any appropriate material and actuating means that act upon a pair of movable jaws (3) that project from one of the ends of said outer housing (2), wherein the actuating means are associated with a tool that is described in greater detail below.

Now making particular reference to the tool that comprises the pair of jaws (3) that interact with one another by means of actuating means comprising a central stationary part and two substantially rectangular cam plates (4), arranged such that said plates are facing both sides of the central stationary part, which are slidable on said central stationary part. The two cam plates (4) are associated with a shaft for driving linear movement (5), which enables the transmission of the user's movement orders to the jaws (3), said jaws being coupled to the central stationary part and the two cam plates, as will be described further below.

Figure 5:
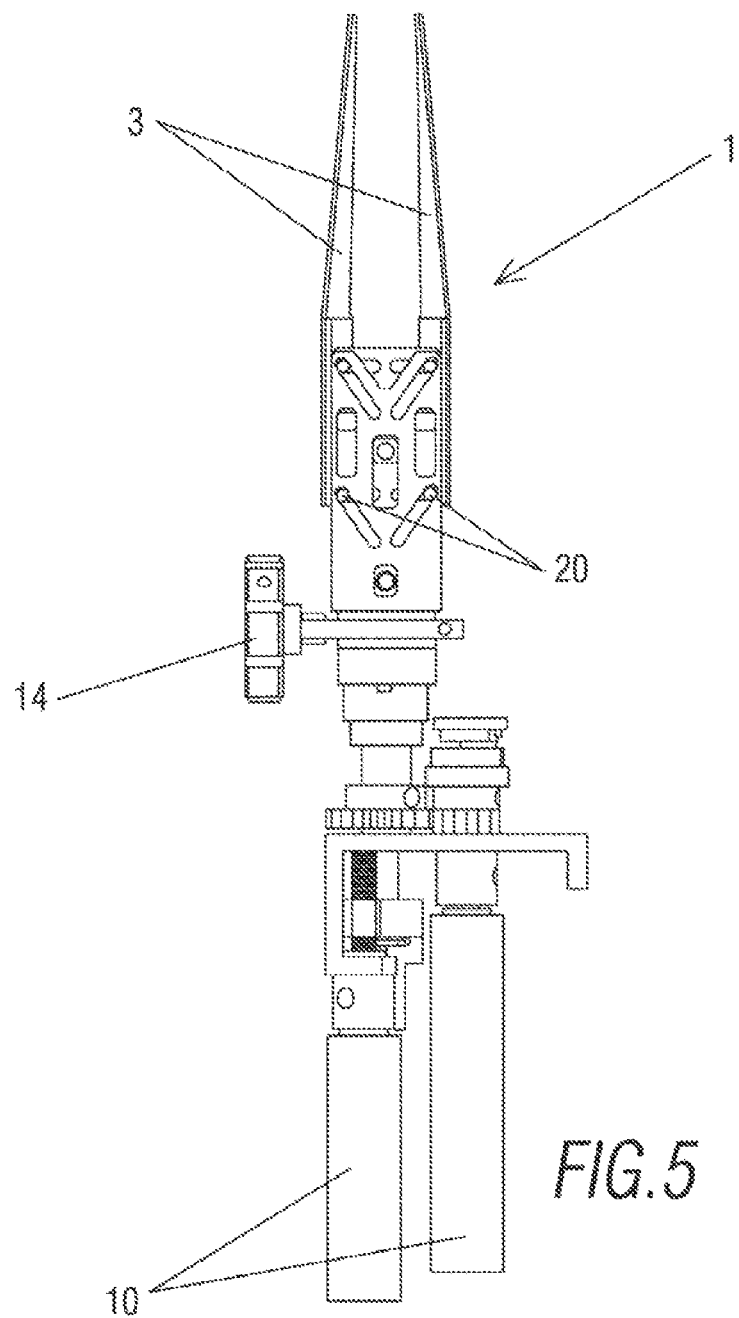
FIG. 5. Shows a side elevational view of the tool of the present invention in a condition such that the jaws are in an open position.
Figure 6:
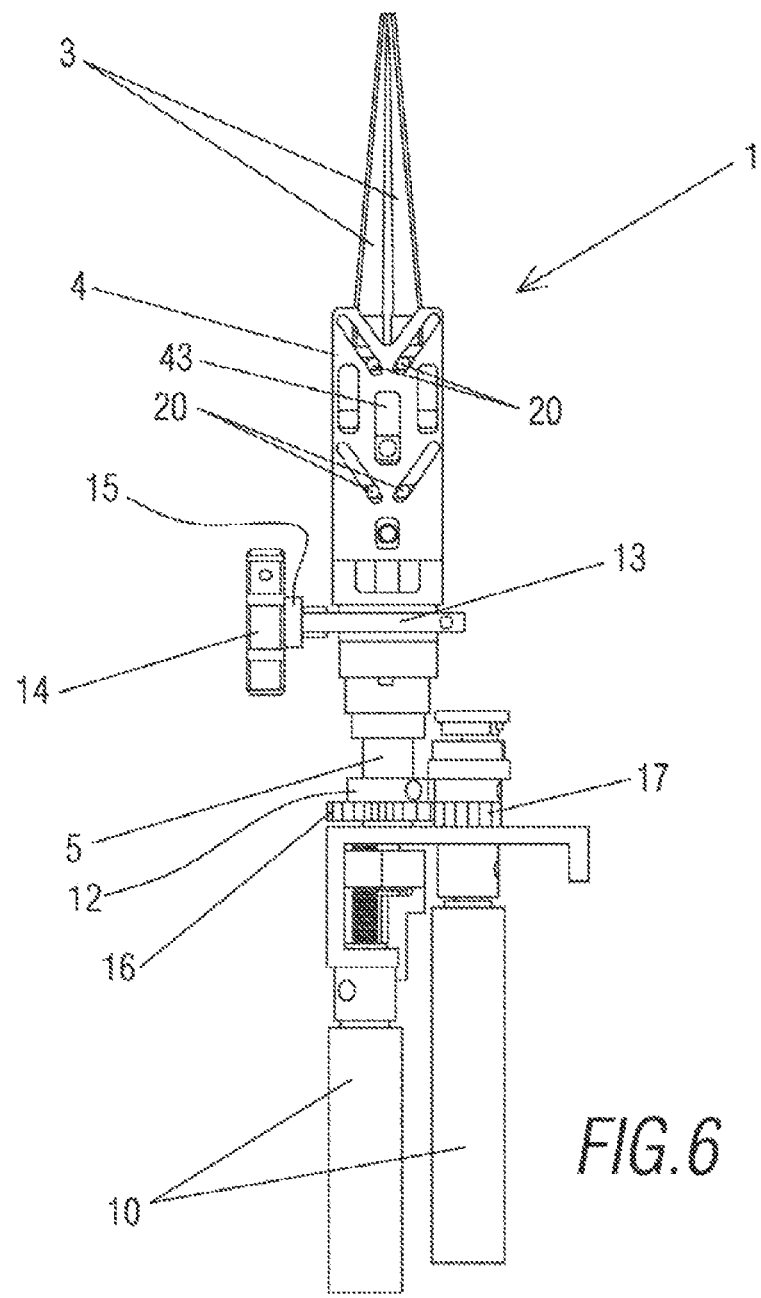
FIG. 6. Shows a side elevational view of a tool of the present invention in a condition such that the jaws are in a closed position.
Figure 7:
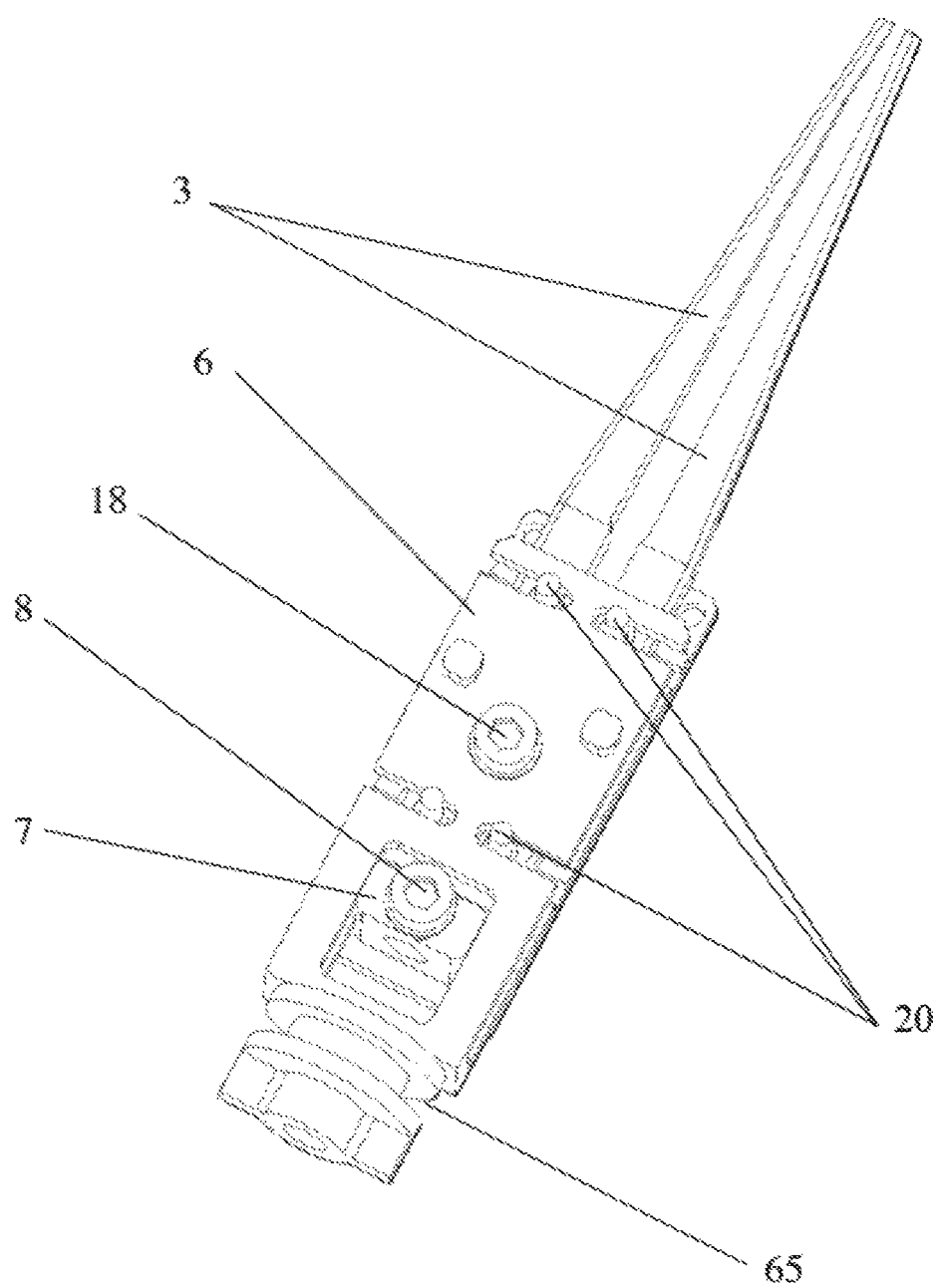
FIG. 7. Shows an additional detailed perspective view of the tool in accordance with the present invention.

Therefore, in a forward movement of the cam plates (4), said plates cause a linear movement away from one jaw respective to the other, i.e. towards an open position (shown in FIG. 5), whereas in a backward movement of the cam plates (4), said plates cause a linear movement for moving one of the jaws (3) closer to the other, i.e. towards a closed or gripping position of an object by means of the jaws (3) (shown in FIG. 6).

Figure 4:
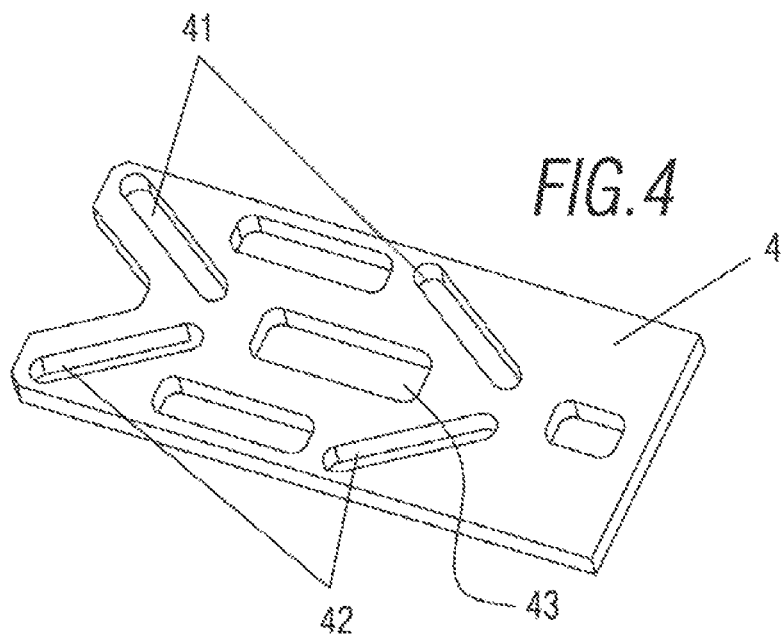
FIG. 4. Shows a detailed perspective view corresponding to one of the cam plates.

As can be more clearly observed in FIG. 4, each of the cam plates (4) has a pair of upper linear slots (41) and a pair of lower linear slots (42) that converge respectively at a point near the central longitudinal axis of the cam plate (4), in whose upper and lower slots (41, 42), respectively, protuberances (20) in the form of stubs that project from each of the jaws (3) are slidable.

Figure 3:
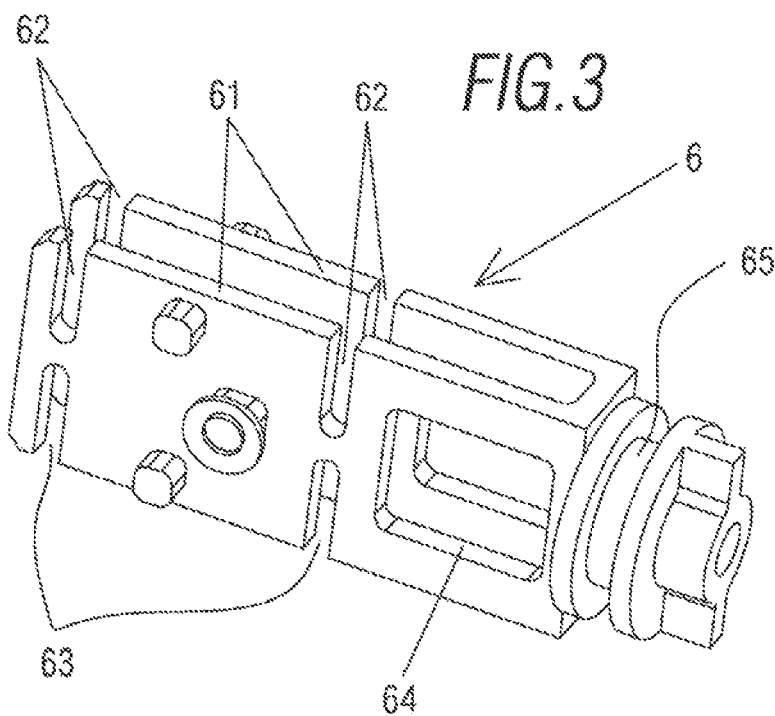
FIG. 3. Shows a detailed perspective view of the central stationary part that forms part of the tool.

Returning to the central stationary part and with special reference to FIG. 3, it comprises a substantially U-shaped body (6) wherein each of its side flaps (61) include a pair of upper grooves (62), separate and parallel therebetween, and a pair of lower grooves (63), separate and parallel therebetween, wherein the protuberances (20) that project from each of the jaws (3) are slidable, whose upper and lower grooves (62, 63) extend from a central part of the side flaps (61) in the direction of the upper and lower rim, respectively.

The two cam plates (4) are joined together through an intermediate piece (7) which has a substantially cubic shape that is coupled to the linear actuation axis (5). Said intermediate piece (7) can be moved through guiding means disposed on the substantially U-shaped body (6). Such guiding means consist of a window (64) disposed on each of the flaps (61) that compose the substantially U-shaped body (6), as can be more clearly observed in FIG. 3.

This intermediate piece (7) and the two cam plates (4) are held together by means of pins (8) that pass through a through hole disposed in the intermediate piece and through holes present in the two cam plates (4).

In order to soften the approximation and/or separation movement of the jaws (3), a helical spring (9) is provided which is housed in a hole disposed in a region located between the two flaps of the substantially U-shaped body (6), wherein each of the ends of the helical spring (9) is in contact with a corresponding jaw (3).

The actuating means include small electric motors (10) housed in the interior of the outer housing (2) and which are powered by a battery (not shown), which can be started up by means of a user interface disposed on the outer side of the outer housing (2). The user interface consists of tactile pushbuttons (11) arranged on one side of the outer housing (2) and a screen or display (19), although a touch screen with virtual pushbuttons may also be used.

In order to enable a rotary movement of the jaws (3), the actuating means include a rotating shaft (12) solidly coupled to the substantially U-shaped body (6), such that when the rotating shaft (12) rotates driven by an electric motor (10) it transmits the movement to the substantially U-shaped body (6).

Advantageously, the rotating shaft (12) is internally hollow, in whose interior the shaft for driving linear movement (5) is concentrically arranged.

Should it be necessary to separate the tool from the rest of the grip device (2), for example, due to the replacement of the jaws (3) or due to malfunction, removable blocking means shall be provided to maintain the central stationary part joined to the rotating shaft. These removable blocking means consist of a pin fitted with a grip section formed by two parallel rods (13) on one end which, during operation, are inserted in a circumferentially slotted section (65) present in the rear end of the substantially U-shaped body (6) and a tightening rotating wheel (14), which includes a lower region (15) that stops against the outer side of the outer housing (2).

In order to carry out the rotary movement of the rotating shaft of the actuating means, a gear assembly formed by two cogwheels (16, 17) that engage with each other is disposed in the interior of the outer housing (2), wherein one of the cogwheels is associated with an independent actuator or electric motor (10). Therefore, when the electric motor (10) associated with the cogwheel (17) is actuated it causes the rotation of the cogwheel (17), transmitting the movement to the cogwheel (16) solidly fixed to the rotating shaft (12).

Additionally, the actuating means include a CPU printed circuit board (not shown) disposed in the interior of the outer housing (2) which acts as a control unit and is connected to the user interface and the electric motors (10).

Additionally, mention should also be made of the fact that additional guiding means are provided between the cam plates (4) and the substantially U-shaped body (6), forming an additional longitudinal slot (43) present in each of the cam plates (4), wherein a pin (18) fixed to the substantially U-shaped body, for example by means of a threaded relationship, is inserted (6).

Lastly, mention should be made of the fact that the orientation of the pair of linear upper slots (41) and the pair of linear lower slots (42) in each of the cam plates (4) is such that, in the event of electrical failure or failure of the electronic components, upon manually removing the tool backwards, the jaws open in such a manner as to not damage the interior of a zone to be treated. This aspect is particularly relevant if using this tool (1) as a laparoscopic apparatus.

The details, shapes, dimensions and other accessory elements used in the manufacture of the tool of the invention may be conveniently substituted by others that do not detract from the scope defined by the claims included below.

What is claimed is:

1. A tool comprising a pair of jaws interacting with one another by means of actuating means, characterized in that said actuating means comprise a central stationary part and two cam plates arranged such that said plates are facing both sides of the central stationary part, the cam plates being slidable on said central stationary part, the two cam plates being associated with a shaft for driving linear movement, and wherein the jaws are coupled to the central stationary part and the two cam plates, such that during a forward movement of the cam plates, said plates cause a linear movement away from one jaw respective to the other, during a backward movement thereof, said cam plates cause a linear movement for moving one of the jaws closer to the other, wherein each of the cam plates has a pair of linear upper slots and a pair of linear lower slots that converge respectively at a point near a central longitudinal axis of the cam plates, and wherein protuberances projecting from each of the jaws are slidable in the upper and lower slots.

2. The tool, according to claim 1, wherein the two cam plates are joined together by means of an intermediate piece coupled to a linear driving shaft, said intermediate piece being movable through guiding means disposed on the central stationary part.

3. The tool, according to claim 2, wherein the intermediate piece and the two cam plates have additional fixing means.

4. The tool, according to claim 3, wherein such fixing means comprise through holes disposed in the intermediate piece and the two cam plates in which a pin or screw element is inserted.

5. The tool, according to claim 1, wherein the tool has elastic means disposed between the two jaws.

6. The tool, according to claim 5, wherein the elastic means comprise at least one helical spring housed in the central stationary part.

7. A grip device, for the precision handling of small objects, wherein the grip device comprises the tool, according to claim 1, wherein said tool is actuated by actuating means.

8. The grip device, according to claim 7, wherein the actuating means include electrically motorized means.

9. The grip device, according to claim 7, wherein the grip device includes a user interface connected to the actuating means.

10. The grip device, according to claim 9, wherein the actuating means include a printed circuit board connected to the user interface.

11. The grip device, according to claim 7, wherein the actuating means include a rotating shaft solidly coupled to the central stationary part.

12. The grip device, according to claim 11, wherein the rotating shaft is internally hollow, the shaft for driving linear movement being concentrically arranged inside the rotating shaft.

13. The grip device, according to claim 7, the tool includes removable blocking means for maintaining the central stationary part joined to a rotating shaft.

14. The grip device, according to claim 13, wherein the removable blocking means comprise a pin fitted on one end with a grip section, insertable in a circumferentially slotted section present in the central stationary part of the actuating means and a tightening rotating wheel.

15. The grip device, according to claim 7, wherein rotary movement of a rotating shaft of the actuating means is transmitted by a gear assembly formed by two cogwheels that engage with each other, wherein each cogwheel is associated with an independent actuator.

16. The grip device, according to claim 7, wherein the grip device includes an outer housing wherein the actuating means and, at least partially, the tool, are housed.

17. A tool comprising a pair of jaws interacting with one another by means of actuating means, characterized in that said actuating means comprise a central stationary part and two cam plates arranged such that said plates are facing both sides of the central stationary part, the cam plates being slidable on said central stationary part, the two cam plates being associated with a shaft for driving linear movement and wherein the jaws are coupled to the central stationary part and the two cam plates, such that during a forward movement of the cam plates, said plates cause a linear movement away from one jaw respective to the other, during a backward movement thereof, said cam plates cause a linear movement for moving one of the jaws closer to the other, and wherein the central stationary part comprises a substantially U-shaped body that includes side flaps, each having a pair of upper grooves and a pair of lower grooves in which the protuberances that project from each of the jaws are slidable, and wherein the upper and lower grooves extend from a central part of the side flaps in the direction of upper and lower rims, respectively.

18. A tool comprising a pair of laws interacting with one another by means of actuating means, characterized in that said actuating means comprise a central stationary part and two cam plates arranged such that said plates are facing both sides of the central stationary part, the cam plates being slidable on said central stationary part, the two cam plates being associated with a shaft for driving linear movement and wherein the laws are coupled to the central stationary part and the two cam plates, such that during a forward movement of the cam plates, said plates cause a linear movement away from one jaw respective to the other, during a backward movement thereof, said cam plates cause a linear movement for moving one of the jaws closer to the other, wherein the two cam plates are joined together by means of an intermediate piece coupled to a linear driving shaft, said intermediate piece being movable through guiding means disposed on the central stationary part, and wherein the guiding means comprise a window disposed on each of side flaps of a substantially U-shaped body.

* * * * *